United States Patent [19]
Johnson et al.

[11] 3,985,783
[45] Oct. 12, 1976

[54] PROCESS FOR RING ACYLATION OF PHENOLS

[75] Inventors: Francis Johnson, Long Island City, N.Y.; Renato Cricchio, Varese, Italy

[73] Assignee: The Dow Chemical Company, Midland, Mich.

[22] Filed: June 9, 1975

[21] Appl. No.: 585,229

[52] U.S. Cl. .......................... 260/465 F; 260/335; 260/473 S; 260/571; 260/575; 260/591; 260/592
[51] Int. Cl.² ................. C07C 49/82; C07C 69/95; C07C 121/75
[58] Field of Search ............... 260/591, 592, 465 F, 260/473 S, 570 AB, 571, 575

[56] References Cited
OTHER PUBLICATIONS

Ohah: Friedel–Crafts and Related Reactions, vol. III, pp. 46–47, Interscience Publishers, New York (1964).
Runge et al.: Angew. Chem., 68, p. 618 (1956).

*Primary Examiner*—Lewis Gotts
*Assistant Examiner*—Dolph H. Torrence
*Attorney, Agent, or Firm*—Theodore Post; C. Kenneth Bjork

[57] ABSTRACT

Mono- and poly-phenols and derivatives thereof are ring acylated by a Friedel-Crafts acylation reaction in which the hydroxy groups are protected by prior silylation.

3 Claims, No Drawings

PROCESS FOR RING ACYLATION OF PHENOLS

BACKGROUND OF THE INVENTION

The ring acylation of phenols is almost impossible to achieve in good yields. Suitable methods for the C-acylation of phenols of the resorcinol and phloroglucinol type do not exist in a general sense. As aptly pointed out by E. Berliner, "Organic Reactions," Vol. V, pages 236–7, John Wiley & Sons Inc., New York, 1949, direct acylation of phenols by a Friedel-Crafts procedure is not particularly advantageous, because complex mixtures of C-acylated and O-acylated compounds are generally obtained. The Houben-Hoesch reaction, which is described by the authors in Ber. 48, 1122, 1915 and Ber. 59, 2878, 1926, runs fairly smoothly, particularly with polyphenols, but has considerable disadvantages as well, e.g., the use of nitriles which lead to the formation of appreciable amounts of by-product iminoethers. The Fries rearrangement, described in detail by A. H. Blatt, "Organic Reactions," Vol. 1, 342, John Wiley & Sons Inc., New York, 1942, is a good method for obtaining o-acyl and p-acylphenols, generally as a mixture of the two products, in which the proportions of both isomers depend on reaction conditions, but this rearrangement is practically of minor importance if C-acylated polyphenols, more particularly if C-acylated polyphenols substituted in the ring with other groups, are desired.

A suitable method for preparing C-acylated polyphenols involves first protecting the hydroxy groups by transforming them into methoxy groups by reaction with dimethyl sulfate or diazomethane, as reported by Saul Patai, "The Chemistry of the Hydroxyl Group," Part 2, page 1006, John Wiley & Sons, 1971, subsequent acylation being carried out according to known procedures, and subsequent restoration of the free hydroxy groups by a usual demethylation process. Because of the number of steps which are involved, this method is quite tedious and cumbersome. Moreover, complete demethylation is difficult to achieve.

SUMMARY OF THE INVENTION

We have now discovered a new and useful synthetic route for the C-acylation of mono- and polyphenols and derivatives thereof which avoids the disadvantages of the prior art. The new synthetic route is a two-step process in which the phenolic compound is first converted to the corresponding silyl ether to protect the hydroxy groups by reaction with a suitable silylating agent, as hereinafter defined, then is C-acylated under usual Friedel-Crafts reaction conditions. The great advantage is that the silyl group or groups are lost during the workup of the reaction mixture, so that the C-acylated phenolic compound is obtained directly from the acylation reaction.

Pursuant to the inventive process, it is possible to obtain in good yield compounds of the general formula

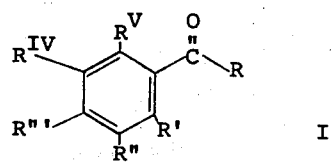
I wherein $R'$, $R''$, $R'''$, $R^{IV}$ and $R^V$ are independently selected from the group consisting of hydrogen, hydroxy, $(C_{1-3})$-alkyl, $(C_{1-3})$-alkoxy and carbo-$(C_{1-3})$-alkoxy, with the proviso that at least one of $R'$ and $R'''$ is hydroxy; R is a $(C_{1-3})$-alkyl radical or the group

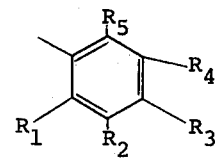

wherein the substituents $R_1$ through $R_5$ are independently selected from hydrogen, $(C_{1-3})$-alkyl, $(C_{1-3})$-alkoxy, benzyloxy, hydroxy, halo, nitro, cyano and amino.

Some of the compounds of formula I above are precursors to naturally occurring, and often biologically active, xanthones, e.g. guanandin, gentisin, isoathyriol, swertianol and griseofulvin. Furthermore, the compounds of formula I wherein $R'$ is hydroxy and R is the group

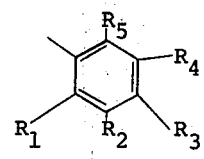

wherein $R_1$ represents halo, nitro or $(C_{1-3})$-alkoxy may be cyclized to xanthones of the following formula

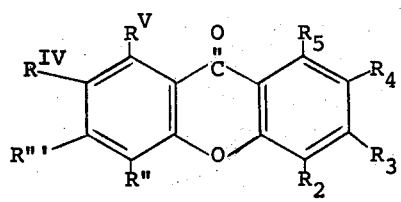

Some of these cyclization reactions will be described in the Examples.

Several 2-hydroxybenzophenone derivatives having valuable antimicrobial and disinfectant properties are known from Dutch Patent Application Nos. 64.05517 and 68.08420 and from Swiss Pat. No. 500.663. U.S. Pat. No. 3,267,148 describes the preparation of 2-methoxybenzophenone compounds which are useful intermediates for the synthesis of the antifungal substance, griseofulvin. The 2,4-dihydroxybenzophenones reported in U.S. Pat. No. 3,769,349 are employed as U.V. ray absorbing agents. Other 2-hydroxybenzophenones and their condensation products with ethylenediamine are excellent chelating agents for a variety of metals, as described in U.S. Pat. No. 3,136,817.

In the process of this invention, a phenolic substrate of the general formula

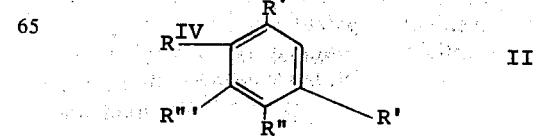
II wherein R' through R$^V$ have the meanings given above, is converted to the corresponding O-silyl derivative by means of a suitable silylating agent, which is advantageously selected from a compound of one of the formulas

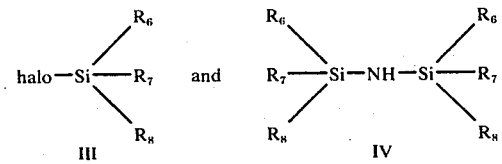

wherein halo represents chloro or bromo and each of the groups $R_6$, $R_7$ and $R_8$ independently represents a lower alkyl radical of 1 to 4 carbon atoms or a phenyl group. Suitable silylating agents of above formulas III and IV may be, among others, butyldimethylchlorosilane, triphenylchlorosilane, methyldiphenylchlorosilane, triethylchlorosilane, trimethylbromosilane, trimethylchlorosilane, ethyldipropylbromosilane, diethylmethylbromosilane, dimethylpropylchlorosilane, tripropylbromosilane, butylethylmethylbromosilane, tripropylchlorosilane and 1,1,1,3,3,3-hexamethyldisilazane, 1,1,1-butyldimethyl-3,3,3-trimethyldisilazane, 1,1,1-triethyl-3,3,3-trimethyldisilazane or 1,1,1-propylethylmethyl-3,3,3-diethylmethyldisilazane.

In carrying out the inventive process, a molar proportion of the phenolic compound of formula II is contacted with at least $n$ molar proportions of a silane of formula III or IV, wherein $n$ is an integer which identifies the number of hydroxy groups in the phenolic compound which require protection before carrying out the acylation reaction. Since it has been found that the O-silylation reaction proceeds more smoothly if a compound of formula III or IV is employed in a large molar excess over the required stoichiometric amount, an excess of compound III or IV is preferred.

When a compound of formula III is used as the silylating agent, the reaction is preferably carried out in the presence of an organic base as acid acceptor of the by-product hydrogen halide which forms, and which base is advantageously selected from the tertiary nitrogen organic bases such as, for instance, triethylamine, pyridine, picoline and the like. When pyridine or a lower alkyl derivative thereof is used, it can also act as the reaction solvent.

When a compound of formula IV is used as the silylating agent, it has been found that the formation of a silyl ether of a phenolic compound of formula II occurs more smoothly if the reaction is carried out in the presence of a small amount of an acidic catalyst, which is preferably selected from a compound of formula III wherein the hydrocarbyl substituents on the silicon atom are the same as those on the silicon atoms of the disilazane compound.

The temperature of reaction is not critical. It has been found that the phenolic compound is usually easily converted to the corresponding O-silyl derivative at room temperature; but for sluggish reactions, gentle heating is conveniently applied. The silyl ether is obtained in substantially quantitative yield. The phenolic silyl ethers are oily distillable substances and are recovered from the reaction mixture by distillation under reduced pressure. However, they may also be used in the crude state for the subsequent acylation step without substantially impairing the overall yield.

The so-obtained silyl ether is acylated on the benzene ring using standard Friedel-Crafts reaction conditions, and the silyl group or groups are lost during the work-up procedure, so that the C-acylated phenol is obtained directly from the acylation reaction.

The acylating agent is represented by a compound of the formula R-COY, wherein R has the meaning given above and Y represents halo, e.g., chloro or bromo, hydroxy, ($C_{1-3}$)-alkoxy or the group

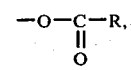

R being defined as above. The solvent and the catalyst which are used in the Friedel-Crafts acylation step are those commonly employed in a Friedel-Crafts reaction. Suitable catalysts are, for instance, an aluminum trihalide, a stannic tetrahalide, a titanium tetrahalide, zinc chloride, boron trifluoride and analogs thereof. Suitable solvents are inert organic solvents, e.g., halogenated ($C_{1-3}$) hydrocarbons, nitromethane, nitrobenzene, carbon disulfide, tetrahydrofuran and the like.

The temperature of acylation is not critical and is conventionally chosen in the range of 0–100° C. The acylation is complete within an interval of time varying from 5 minutes to 48 hours, depending on the nature of the substrate to be acylated.

The proportions of reactants and Friedel-Crafts catalysts are not critical. Although they may be varied within a very wide range, it has been found that particularly good results are obtained when the O-silylated phenolic compound is contacted with at least two molar proportions of the acylating agent, R—COY. Although the amount of catalyst is not critical, it is preferably used in a large molar excess over the acylating agent.

The compounds of the inventive process are then recovered following procedures which are entirely familiar to an art-skilled person. The products are white, crystalline solids.

The yields of the acylation step vary from about 50 to about 90 percent and depend on such factors as the nature of the catalyst, the temperature and reaction time and, chiefly, the substrate to be acylated. While the intermediate O-silyl derivatives are obtained in substantially quantitative yields, the overall yields of the complete process range from 50 to about 90 percent of the desired end product.

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

EXAMPLE I 2,4,6-Trihydroxyphenyl-2'-chlorophenyl ketone (A) To a solution of 80 ml. (0.637 mole) of trimethylchlorosilane in 40 ml. of anhydrous pyridine, 12.6 g. (0.126 mole) of phloroglucinol is added and the mixture is stirred overnight at room temperature. 40 milliliters of benzene is added and the mixture is filtered, concentrated, and distilled under reduced pressure. 50 Grams of O,O,O-tris(trimethylsilyl)phloroglucinol (88%) is recovered. B.p. 94°–96° C/0.01 mm Hg.

(B) A solution of 1.75 g. (0.01 mole) of o-chlorobenzoyl chloride and 5.2 g. (0.02 mole) of stannic chloride in 50 ml. of methylene chloride is prepared in a 250 ml. flask equipped with magnetic stirrer and drying tube. Then 3.42 g. (0.01 mole) of O,O,O-tris(trimethylsilyl)phloroglucinol is added over a period of 2 minutes and the resulting solution is stirred overnight at ambient temperature. The reaction mixture is filtered and the filtrate is twice washed with 50 ml. of concentrated hydrochloric acid. The organic layer is separated, washed twice with 50 ml. of a saturated solution of sodium bicarbonate and dried. A solid residue is obtained which is recrystallized from ethanol. Yield 2.2 g. (80%). M.p. 141°–43° C.

A sample of the product of Example I (B) when acetylated with an acetic anhydride-pyridine mixture gives a crystalline triacetate. M.p. 99°–100° C.

EXAMPLE II 2,4,6-Trihydroxy-2',6'-dimethoxybenzophenone

To a solution of 8.0 g. (0.04 mole) of 2,6-dimethoxybenzoyl chloride and 13 g. (0.05 mole) of anhydrous stannic chloride in 50 ml. of methylene chloride, 6.8 g. (0.02 mole) of O,O,O-tris(trimethylsilyl)phloroglucinol is added at room temperature over a period of 5 minutes. After refluxing for two hours, the reaction mixture is extracted with ethyl acetate and the so-obtained organic solution is evaporated to dryness. A red viscous oil is obtained which is triturated with ether until a yellow-white solid forms. The titular product is recovered by filtration and recrystallized from a mixture of ethanol and ethyl acetate. Yield 7.4 grams (64%). M.p. 195°–202° C. (decomp.)

The following examples describe the preparation of other compounds falling within the scope of formula I. They are synthesized according to the procedure of paragraph (B) of Example I, i.e., by reacting equimolecular proportions of the O-trimethylsilyl derivative and the acyl chloride, in the presence of two molar proportions of the Friedel-Crafts catalyst. The preparation of the intermediate O-trimethylsilyl compounds is achieved pursuant to the procedure of paragraph (A) of Example I. The boiling points of these intermediates are given, if they have been isolated and characterized, otherwise they are useful in the prepared crude state. The reported percent yields are calculated from the starting phenolic compound and are therefore the overall yields of the process.

EXAMPLE III 2,4,6-Trihydroxy-2',4'-dichlorobenzophenone from O,O,O-tris(trimethylsilyl)phloroglucinol and 2,4-dichlorobenzoyl chloride in the presence of stannic chloride. Yield 76% (oily product, not distillable).

EXAMPLE IV

4-Hydroxy-2'-chlorobenzophenone from O-trimethylsilylphenol (b.p. 91° C/0.5 mm Hg) and 2-chlorobenzoyl chloride in the presence of aluminum trichloride. Yield 54%. M.p. 102°–4° C. (from ethanol)

EXAMPLE V 2,4-Dihydroxy-2'-chlorobenzophenone from O,O-bis(trimethylsilyl)resorcinol and 2-chlorobenzoyl chloride in the presence of stannic chloride. Yield 80%. M.p. 131°–2° C. (from ethyl acetate/ethanol)

EXAMPLE VI 2,5-Dihydroxy-2'-chlorobenzophenone from O,O-bis(trimethylsilyl)hydroquinone and 2-chlorobenzoyl chloride in the presence of stannic chloride. Yield 84%.

EXAMPLE VII

4-Hydroxy-2'-nitrobenzophenone from O-(trimethylsilyl)phenol and 2-nitrobenzoyl chloride in the presence of stannic chloride. Yield 56%. M.p. 165°–67° C. (from ethanol)

EXAMPLE VIII 2,4-Dihydroxyacetophenone from O,O-bis(trimethylsilyl)resorcinol and acetyl chloride in the presence of titanium tetrachloride. Yield 80%. M.p. 97°–8° C. (from methanol)

The following two examples describe the cyclization of the compounds of Examples 1 and 3 to the corresponding xanthones.

EXAMPLE IX 1,3-Dihydroxyxanthone 35 Grams (0.133 mole) of 2,4,6-trihydroxyphenyl-2'-chlorophenyl ketone are added to a solution of 56 g. of potassium hydroxide in 400 ml. of water and the solution is then heated on a steam bath for 4 hours. The resulting dark solution is cooled and acidified with hydrochloric acid. The titular product is extracted by means of ethyl acetate (4 × 100 ml.). The latter extract is washed with a little water than dried over magnesium sulfate. Removal of the ethyl acetate affords essentially pure 1,3-dihydroxyxanthone (16 g.) as a faintly yellow powder (53% yield). M.p. 259° C. (from methanol).

EXAMPLE X 1,3-Dihydroxy-6-chloroxanthone 4.75 Grams (0.0159 mole) of 2,4,6-trihydroxyphenyl-2',4'-dichlorophenyl ketone is added to a solution of 2.8 g. of potassium hydroxide in 50 ml. of water and the mixture heated on a steam bath for 4 hours. The mixture is acidified with hydrochloric acid and extracted with ethyl acetate (500 ml.). The extract is washed with saturated sodium bicarbonate solution, then with water and subsequently evaporated to dryness. The highly insoluble residue (1.63 g.) is substantially pure 1,3-dihydroxy-6-chloroxanthone. Crystallization of a sample from ethanol affords the pure compound. M.p. 333°–5° C.

The starting phenolic compounds and the acyl chlorides are commercially available products.

Typical compounds which can be prepared according to the methods described in Examples I-VIII are:
  2'-Chloro-2,6,3'-trihydroxybenzophenone
  2,6,3'-Trihydroxy-2'-nitrobenzophenone
  2,4,6,5'-Tetrahydroxy-2'-methoxybenzophenone
  2'-Chloro-2,4,6,5'-tetrahydroxy-4'-methoxybenzophenone
  2,4,6,5'-Tetrahydroxy-2'-nitrobenzophenone
  2,4,6,3'-Tetrahydroxy-2',6'-dimethoxybenzophenone 2,4,6,3'-Tetrahydroxy-6'-methoxy-2'-nitrobenzophenone
2'-Benzyloxy-3'-chloro-4-hydroxy-2,4',6'-trimethoxy- 6-methylbenzophenone
2,4,6-Trihydroxypropiophenone
2,6-Dihydroxypropiophenone
2,6-Dihydroxy-4-methoxybutyrophenone
2'-Cyano-2,6-dihydroxybenzophenone
2',4'-Diamino-2-hydroxy-6-methylbenzophenone

What is claimed is:

1. An improved process for ring acylating a phenolic compound of the general formula

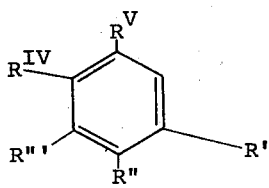

wherein R', R'', R''', $R^{IV}$ and $R^V$ are independently selected from the group consisting of hydrogen, hydroxy, $(C_{1-3})$-alkyl, $(C_{1-3})$-alkoxy and carbo-$(C_{1-3})$-alkoxy, with the proviso that at least one of R' and R''' is hydroxy; which comprises reacting a molar proportion of the above phenolic compound with a silylating agent selected from a compound of one of the following formulas

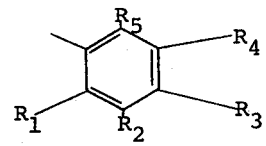

wherein halo is chloro or bromo and each of the groups $R_6$, $R_7$ and $R_8$ independently represents $(C_{1-4})$-alkyl or phenyl, in a molar proportion at least corresponding to the number of the hydroxy groups of the phenolic compound, at room temperature, in the presence of an organic tertiary nitrogen base as acid acceptor when a silylating agent of formula II is employed, then acylating the so-obtained O-silyl derivative with a compound of the formula R-COY, wherein R is $(C_{1-3})$-alkyl or the group

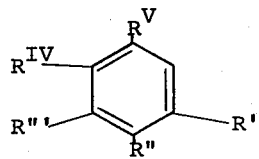

wherein the substituents $R_1$ through $R_5$ are independently selected from hydrogen, $(C_{1-3})$-alkyl, $(C_{1-3})$-alkoxy, benzyloxy, hydroxy, halo, nitro, cyano and amino and Y represents chloro, bromo, hydroxy, $(C_{1-3})$-alkoxy or the —OCOR group in the presence of a catalyst selected from the group of aluminum halides, stannic halides, titanium tetrachloride, zinc chloride and boron trifluoride, in the presence of an inert organic solvent at a temperature varying from 0° C. to 100° C. for a period of time between about 5 minutes and about 48 hours.

2. A process for preparing a compound of the following formula

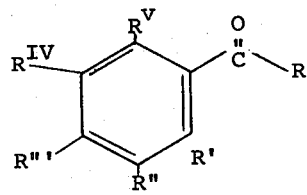

wherein R', R'', R''', $R^{IV}$ and $R^V$ are independently selected from the group consisting of hydrogen, hydroxy, $(C_{1-3})$-alkyl, $(C_{1-3})$-alkoxy and carbo-$(C_{1-3})$-alkoxy, with the proviso that at least one of R' and R''' is hydroxy; R is a $(C_{1-3})$-alkyl radical or the group

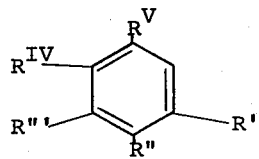

wherein the substituents $R_1$ through $R_5$ are independently selected from hydrogen, $(C_{1-3})$-alkyl, $(C_{1-3})$-alkoxy, benzyloxy, hydroxy, halo, nitro, cyano and amino; which comprises reacting a molar proportion of a phenolic compound of the formula

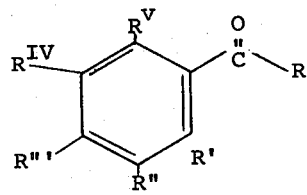

wherein R', R'', R''', $R^{IV}$ and $R^V$ have the above meanings, with a silylating agent selected from a compound of one of the following formulas

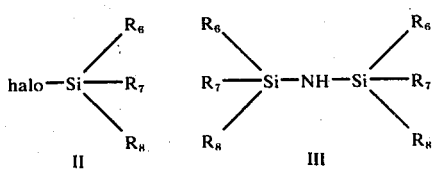

wherein halo is chloro or bromo and each of the groups $R_6$, $R_7$ and $R_8$ independently represents $(C_{1-4})$-alkyl or phenyl, in a molar proportion at least corresponding to the number of the hydroxy groups of the phenolic compound, at room temperature, in the presence of an organic tertiary nitrogen base as acid acceptor when a silylating agent of formula II is employed, and in the presence of a compound of formula II as an acidic catalyst when a silylating agent of formula III is employed, then acylating the so-obtained O—silyl derivative with a compound of the formula R—COY, wherein R has one of the above meanings and Y represents halo, hydroxy, $(C_{1-3})$-alkoxy or the —OCOR group in the presence of a catalyst selected from the group of aluminum halides, stannic halides, titanium tetrachloride, zinc chloride and boron trifluoride, in the presence of an inert organic solvent at a temperature varying from 0° C. to 100° C. for a period of about 5 minutes to about 48 hours.

3. An improved process for ring acylating a phenolic compound of the general formula

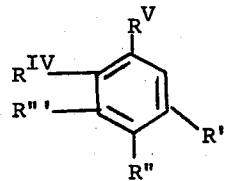

wherein R', R'', R''', R$^{IV}$ and R$^{V}$ are independently selected from the group consisting of hydrogen, hydroxy, (C$_{1-3}$)-alkyl, (C$_{1-3}$)-alkoxy and carbo-(C$_{1-3}$)-alkoxy, with the proviso that at least one of R' and R''' is hydroxy; which comprises reacting a molar proportion of the above phenolic compound with a silylating agent of the following formula

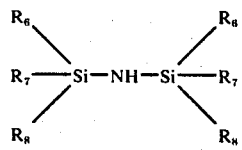

wherein each of the groups R$_6$, R$_7$ and R$_8$ independently represents (C$_{1-4}$)-alkyl or phenyl, in a molar proportion at least corresponding to the number of the hydroxy groups of the phenolic compound, at room temperature, in the presence of a compound having the formula

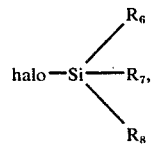

wherein halo is chloro and R$_6$, R$_7$ and R$_8$ are for the same substituents as in the silylating agent of the given formula, as an acidic catalyst, then acylating the so-obtained O—silyl derivative with a compound of the formula R—COY, wherein R is (C$_{1-3}$)-alkyl or the group

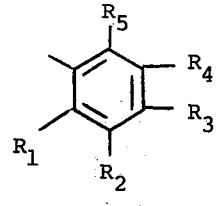

wherein the substituents R$_1$ through R$_5$ are independently selected from hydrogen, (C$_{1-3}$)-alkyl, (C$_{1-3}$)-alkoxy, benzyloxy, hydroxy, halo, nitro, cyano and amino and Y represents chloro, bromo, hydroxy, (C$_{1-3}$)-alkoxy or the —OCOR group in the presence of a catalyst selected from the group of aluminum halides, stannic halides, titanium tetrachloride, zinc chloride and boron trifluoride, in the presence of an inert organic solvent at a temperature varying from 0° C. to 100° C. for a period of time between about 5 minutes and about 48 hours.

* * * * *